US005460837A

United States Patent [19]
D'Amico et al.

[11] Patent Number: 5,460,837
[45] Date of Patent: Oct. 24, 1995

[54] PREPARATION AND USE OF A MALOLACTIC FERMENT BIOMASS

[75] Inventors: Nicola D'Amico, Yverdon; Thang H. Dac, Le Mont s/Lausanne; Tomaso Sozzi; Robert D. Wood, both of Lausanne, all of Switzerland

[73] Assignee: Nestec S.A., Vevey, Switzerland

[21] Appl. No.: 233,554

[22] Filed: Apr. 26, 1994

Related U.S. Application Data

[63] Continuation of Ser. No. 850,093, Mar. 12, 1992, abandoned.

[30] Foreign Application Priority Data

Apr. 16, 1991 [CH] Switzerland ............................. 1138/91

[51] Int. Cl.$^6$ ..................................................... C12G 1/00
[52] U.S. Cl. .................. 426/11; 426/14; 426/15; 426/592
[58] Field of Search ................................... 426/11, 12, 15, 426/14, 16, 7, 590, 592; 435/139, 252.1, 253.6, 260

[56] References Cited

U.S. PATENT DOCUMENTS

| | | |
|---|---|---|
| 4,380,552 | 4/1983 | Gestrelius et al. . |
| 4,547,373 | 10/1985 | Sandine et al. . |
| 4,562,077 | 12/1985 | King . |
| 4,626,437 | 2/1990 | Lang et al. . |
| 4,902,518 | 2/1990 | Lang et al. ................................. 426/14 |
| 5,104,665 | 4/1992 | Fleet et al. ................................. 426/15 |

FOREIGN PATENT DOCUMENTS 0327380  8/1989  European Pat. Off. .

OTHER PUBLICATIONS

Beelman, "Development and Utilization of Starter Cultures to Induce Malolactic Fermentation in Red Table Wines," Proceedings of the U.C.D. Grape & Wine Centennial Symposium, University of California, Davis pp. 109–117 (1982).
Guillaux–Benatier, et al. "Contribution to the Study of Degradation of L–malic Acid by Lactic Bacteria Isolated from Wine: Stimulating Effect of Yeast Autolysates", Vitis 24, 59–74 (1985) and partial translation thereof.
Edwards, et al., "Inducing Malolactic Fermentation In Wines," Biotechnology Advances, 7, No. 3, 333–360 (1989).
Chemical Abstracts, vol. 108, No. 13, p. 487 Abstract No. 110788u (1988) citing Delfini, et al., Vigneuini 1987, 14(11), 35–38, "Attempts to Stimulate Malolactic Fermentation During and After Alcoholic Fermentation By Using Lyophilized Bacterial Cultures Effect of Alcohol on the Inoculants".
Chemical Abstracts vol. 55, No. 23 column 25154g, citing Fell, Annuaire agr. Suisse 62, 249–64 (1961), "Malic–lactic Fermentation of Wine and the Possibilities of Starting it by Inoculation" European Search Report for Aplication No. 92104158.8 (1992).

*Primary Examiner*—Leslie A. Wong
*Attorney, Agent, or Firm*—Vogt & O'Donnell

[57] ABSTRACT

A malolactic ferment is produced from at least one malolactic bacterium strain which is cultured in a culture medium containing an assimilable nitrogen source, malic acid and alcohol. The ferment biomass is separated from the culture medium. The biomass may be concentrated and may be frozen with a cryoprotective agent or dehydrated. The biomass may be added directly to wine to effect malolactic fermentation.

12 Claims, No Drawings

PREPARATION AND USE OF A MALOLACTIC FERMENT BIOMASS

CROSS REFERENCE TO RELATED APPLICATION

This application is a continuation application of application Ser. No. 07/850,093, filed Mar. 12, 1992, and now abandoned.

BACKGROUND OF THE INVENTION

This invention relates to a process for the production of a malolactic ferment, to the ferment thus obtained and to its use in the production of a wine.

There are various processes for deacidifying wine by malolactic fermentation during which malolactic bacteria, more particularly *Leuconostoc oenos* and certain lactobacilli, convert the malic acid present in the wine into lactic acid.

U.S. Pat. No. 4,380,552, for example, proposes deacidifying a wine by passing it through a bed of gel beads containing viable cells of *Leuconostoc oenos*. However, it is not certain that this process is any better than direct inoculation of the wine with this bacterium.

In European Patent Application Publication No. 327 380, wine is subjected to controlled malolactic fermentation by passage through a vessel containing at least $10^8$ cells of malolactic bacteria per ml and delimited upstream and downstream by filters which retain the bacteria. The same batch of bacteria could be used for a relatively long time in continuous operation or for up to 5 or 6 months by carrying out fermentation in batches. However, both the process and the equipment used appear relatively complicated.

U.S. Pat. No. 4,562,077 proposes reducing the malic acid content of a wine by converting this acid into lactic acid using frozen or freeze-dried ferments containing strains of *Leuconostoc oenos* selected for their good activity in a quantity of $10^8$ to $10^{13}$ cells/ml. However, the proposed ferments have to be specially activated before the wine can be inoculated with them.

U.S. Pat. No. 4,547,373 proposes strains of *Leuconostoc oenos* capable of achieving relatively rapid malolactic fermentation, namely in about 50 to 100 d, for example at a relatively low temperature of approximately 16° to 18° C. and at a relatively low pH value of about 3.1 to 3.2.

In addition, there are commercially available malolactic ferments intended for use in traditional vinification when it is desired to exercise better control over the malolactic fermentation of a must or a wine rich in malic acid. However, almost all these commercial ferments have to be reactivated before use, for example over a period of two days on a particular medium, which complicates the task of the cellarman.

There are also various processes for making so-called light wines, i.e. wines of which the alcohol content is substantially reduced in relation to that of a so-called normal wine which has an alcohol content of approximately 8.5 to 16% by volume (8.5° to 16° alcohol).

U.S. Pat. No. 4,626,437, for example, describes a process for making a light wine in which a normal wine is subjected to an evaporation process to remove alcohol and aromatic constituents, leaving a condensate which is then subjected to fractional distillation to remove an aromatic fraction and the aromatic fraction thus obtained is returned to the wine reduced in alcohol and aromatic constituents. Unfortunately, a light wine made in this way can still have a substantially modified flavour in relation to that of the starting wine.

U.S. Pat. No. 4,902,518 describes a process for making a light wine in which grape juice is separated into a fraction rich in sugar and a fraction poor in sugar, an aromatic fraction is recovered from the fraction rich in sugar and is added to the fraction poor in sugar which is then subjected to traditional fermentation. A light wine made in this way can differ considerably in its flavour from a wine obtained by traditional fermentation of the starting grape juice.

Since the flavour of a wine is significantly influenced or even strengthened by malolactic fermentation during or after alcoholic fermentation, it could be of advantage to subject light wines of the type in question to malolactic fermentation during or after their production. However, this would presuppose control of the malolactic fermentation process.

Accordingly, there is a need for a reliable and effective malolactic ferment which would be capable of initiating and then rapidly completing malolactic fermentation on direct inoculation into a normal or light wine.

SUMMARY OF THE INVENTION

The object of the present invention is to obviate the disadvantages of known deacidification processes and known ferments and to satisfy the need mentioned above for a reliable and effective malolactic ferment so that the production of normal or light wines could be improved.

To this end, the process according to the invention for the production of a malolactic ferment is characterized in that a culture medium containing alcohol, an assimilable nitrogen source and malic acid is prepared, a biomass is prepared by inoculation and culture of at least one strain of malolactic bacterium in the culture medium and the biomass is then separated.

It has surprisingly been found that a ferment prepared in this way can effectively be inoculated directly into a wine in which it immediately initiates vigorous and rapid malolactic fermentation in a reliable and effective manner.

DETAILED DESCRIPTION OF THE INVENTION

To carry out the process according to the invention, the alcohol-containing culture medium may be prepared by alcoholic fermentation of a base medium containing a fermentable sugar, more particularly a fruit juice or an approximately 5 to 15% by weight solution of sucrose, glucose or fructose for example, this juice or this solution additionally containing the assimilable nitrogen source and the malic acid. The alcoholic fermentation process may be carried out using any yeast known for producing alcohol, more particularly yeasts of the type used in oenology and, more particularly, yeasts of the species *Saccharomyces cerevisiae* for example. The base medium may be inoculated at ambient temperature with approximately 1 to 5% by volume of a traditional ferment or with approximately 0.02 to 0.1% by weight of a commercial concentrated ferment of *S. cerevisiae* and then left to ferment, for example for about 1 to 4 d. Since the pH of the base medium is approximately 2.8 to 3.2 after fermentation under these conditions, it may then be adjusted, if necessary, to approximately pH 3–4.5 and preferably to pH 3.4–3.6, for example by addition of a concentrated NaOH solution.

The alcohol-containing culture medium may also be prepared by directly mixing alcohol and water so that the resulting mixture has an alcohol content of approximately 2.5 to 8% by volume for example. This mixture may also contain the assimilable nitrogen source and the malic acid. If the culture medium is prepared in this way, its pH value may also be adjusted to pH 3–4.5 and preferably to pH 3.4–3.6.

Various materials rich in amino acids or polypeptides, such as a yeast extract, a vegetable or animal protein hydrolyzate, a corn steep liquor or ammonium citrate may be used as the assimilable nitrogen source in the culture medium, for example in a quantity of 0.1 to 1% by weight.

The malic acid may be incorporated in the culture medium in a quantity of approximately 0.1 to 2% by weight for example.

It is also possible to add to the culture medium approximately 0.05 to 0.5% by weight glucose in order, if necessary, to facilitate growth of the malolactic bacterium and approximately 1 to 10 mg/l $SO_2$, for example in the form of sodium bisulfite, to induce a resistance of the malolactic bacterium to $SO_2$ or, more precisely, to the $H_2SO_3$ which is formed in the medium as a result of this addition.

The culture medium may be inoculated with approximately 0.5 to 5% of a culture containing approximately $10^7$ to $10^9$ cells of at least one strain of malolactic bacterium per ml. This/these strain(s) may be selected from strains of lactic bacteria which are capable of effecting the malolactic fermentation and of producing an agreeable flavour, such as for example strains of *Leuconostoc oenos*, *Lactobacillus brevis* or *Lactobacillus plantarum*. This/these strain(s) is preferably selected from strains of *Leuconostoc oenos* which may be isolated from wines undergoing their malolactic fermentation in the cellars of wine growers of central Europe and, more particularly, Switzerland for example. Four strains from which a ferment of particularly remarkable quality can be prepared have been selected from numerous preferred strains thus isolated. These four strains of *Leuconostoc oenos* were lodged by way of example in the Collection Nationale de Cultures de Microorganismes (CNCM), Institut Pasteur, 28 rue du Dr Roux, 7524 Paris Cedex 15, France, on the 29.03.91 under the Budapest Treaty and have been given the Nos. CNCM I-1063, I-1064, I-1065 and I-1066. These four strains are very similar to one another and, essentially, are only distinguished from one another by their different sensitivity to phages. Particulars of their morphology and their properties are given in the following.

CNCM I-1064

Morphology:

Gram-positive microorganism, negative catalase and optional anaerobe.

Small spherical cells, occasionally lenticular, in more or less long chains (on MRS medium).

The cells may be elongated or may even be in the form of bacilli on wine (particularly acid wine, pH 3.0–3.2).

No presence of flagellae, no spore formation.

Fermentation of sugars:

Production of acid from glucose.

Others:

Ability to ferment the malate into L(+) lactic acid in the presence of alcohol (malolactic fermentation)

CNCM I-1063, I-1065 and I-1066

The morphology and properties of each of these strains are the same as those described above for the strain CNCM I-1064.

The said lactic bacterium strain can be cultivated in the said culture medium at ambient temperature, in other words at a temperature of around 18° to 30° C., over a period of about 1 to 4 d until the medium contains approximately $10^7$ to $10^9$ cells/ml.

The biomass thus obtained may then be separated and, if necessary, concentrated approximately 20 to 100 times, for example by ultrafiltration or centrifugation.

After it has been separated and, if necessary concentrated, the biomass may be dehydrated, more particularly by freeze-drying for example. In a preferred embodiment, it is frozen after the addition of a cryoprotective agent, such as glycerol for example, and after pH adjustment to approximately 4.2 to 4.8.

The malolactic ferment thus obtained may contain approximately $5.10^8$ to $10^{11}$ cells/g. It may be used for converting malic acid into lactic acid during the production of a wine. It is distinguished by its ability to initiate malolactic fermentation on direct inoculation into a wine and is capable of rapidly completing this fermentation process.

In addition to the use of the ferment in the production of a so-called normal wine, the present invention also relates to its use in the production of a so-called light wine.

Thus, the present invention relates more particularly to the use of the ferment according to the invention in a first particular process for the production of a light wine comprising partial separation of sugar from a grape must, more particularly by ultrafiltration, alcoholic fermentation of the sugar-reduced must and malolactic fermentation of the low-alcohol wine thus obtained.

The present invention also relates to the use of the ferment according to the invention in a second particular process for the production of a light wine comprising at least partial alcoholic fermentation of a grape must, at least partial elimination of the alcohol produced during this alcoholic fermentation and malolactic fermentation and/or secondary alcoholic fermentation of the low-alcohol wine thus obtained.

For these uses, the ferment according to the invention may be directly inoculated in a quantity of approximately 0.01 to 0.1% by weight into a wine at approximately 18° to 30° C. which has a total $SO_2$ content below about 50 mg/l and a suitable pH, depending on its alcohol content. For a so-called normal wine having an alcohol content of approximately 8.5 to 16% by volume, this suitable pH may be approximately 3.1 to 4.5. For a so-called light wine having an alcohol content of approximately 0.5 to 8.5% by volume, this suitable pH may be approximately 2.6 to 4.0.

EXAMPLES

The process for the production and the uses of the malolactic ferment according to the invention are illustrated by the following Examples in which percentages and parts are by weight, unless otherwise indicated.

Example 1

A base medium is prepared in the form of an aqueous 10% solution of sucrose additionally containing 0.5% yeast extract, 0.5% corn steep liquor and 0.5% malic acid. This base medium is inoculated with 2% by volume of a commercial wine-making yeast of *Saccharomyces cerevisiae* and is then left to ferment for 3 d at ambient temperature.

A culture medium having an alcohol content of 6.2% by volume and a pH of 3.1 is thus obtained, its pH being adjusted to 3.4 by addition of a 20% aqueous NaOH solution. 3 mg/l $SO_2$ in the form of sodium bisulfite and 0.1% glucose are then added.

The culture medium is then inoculated with 3% by volume of a culture containing approximately $10^7$ cells/ml of each of the *Leuconostoc oenos* strains CNCM I-1063, I-1064, I-1065 and I-1066. These strains are cultured in the medium for 3 d at ambient temperature. The biomass of *Leuconostoc oenos* thus obtained is then separated by centrifugation. It is resuspended in a cryoprotective aqueous medium containing 10% glycerol and its pH is adjusted to 4.5. A malolactic ferment is obtained of which the volume is reduced by a factor of 50 in relation to the culture medium and which contains approximately $2.10^9$ cells/ml.

This ferment is frozen by spraying into liquid nitrogen. A frozen ferment is thus obtained in the form of ready-to-use beads containing approximately $2.10^9$ cells of *Leuconostoc oenos* per g.

Example 2

After alcoholic fermentation of a must sulfited with 40 mg $SO_2$/l, a Chasselas wine has an alcohol content of 11.4% by volume, a pH value of 3.39, a tartaric acid content of 3.3 g/l, a malic acid content of 3.2 g/l and a total $SO_2$ content of 10 mg/l.

This wine is inoculated in a 100 l tank with 0.02% by weight frozen beads of the malolactic ferment obtained in Example 1. The development of this inoculated wine is followed in relation to that of the same, but non-inoculated wine in a 100 l tank (for comparison).

A reduction in the malic acid content of the inoculated wine from 3.2 to 2.5 g/l is observed in the first week, from 2.5 to 1.2 g/l in the second week and from 1.2 g/l to virtually 0 g/l between the fourteenth and twenty-third days.

By contrast, it takes about 40 d for the malic acid content of the non-inoculated wine to fall to substantially g/l, the real start of the malolactic fermentation process being delayed by almost 20 d in relation to that of the inoculated wine.

On completion of malolactic fermentation, i.e., after 23 d and 40 d, respectively, the inoculated wine and the non-inoculated wine each contain more than $10^7$ *Leuconostoc oenos* cells per ml. Accordingly, they are as good as one another.

Example 3

A Gamay must was sulfited with 75 mg $SO_2$/l. Its alcoholic fermentation is initiated 5 h later by inoculation with 0.04% by weight of a reactivated suspension of commercial dehydrated yeast of *Saccharomyces cerevisiae*. Fermentation is left to continue for 2 to 3 d at 21° to 29° C. Fermentation is interrupted when the alcohol content reaches 7% by volume.

The pulp is separated for pressing and the partly fermented wine thus obtained is subjected to distillation in vacuo during which volatile aromas are first recovered, after which its alcohol content is reduced to approximately 4 to 5% by volume. The aromas recovered are then returned to the low-alcohol wine thus obtained. In addition, this wine has a pH value of 3.23 and a negligible total $SO_2$ content.

The wine is cooled to 18° C. and inoculated with 1% by volume of a commercial yeast of *Saccharomyces cerevisiae* and with 0.1% by weight of frozen beads of the *Leuconostoc oenos* ferment obtained in Example 1. Malolactic fermentation and secondary alcoholic fermentation are allowed to take place at the same time over a period of 12 d at 18° to 20° C.

The light wine obtained in this way has an alcohol content of 8.2% by volume, a residual malic acid content of substantially zero and an agreeable wine flavour.

We claim:

1. A process for production of a wine comprising inoculating a wine with a frozen malolactic ferment biomass prepared by inoculating a culture medium containing an assimilable nitrogen source, malic acid and alcohol with at least one malolactic bacterium strain, culturing the at least one strain in the medium to obtain a bacteria biomass, separating the biomass from the culture medium, adding a cryoprotective agent to the separated biomass, adjusting the pH of the biomass and cryoprotective agent to a pH of from 4.2 to 4.5 and freezing the pH-adjusted biomass and cryoprotective agent to obtain the frozen biomass.

2. A process for production of a wine comprising inoculating a wine with a dehydrated malolactic ferment biomass prepared by inoculating a culture medium containing an assimilable nitrogen source, malic acid and alcohol with at least one malolactic bacterium strain, culturing the at least one strain in the medium to obtain a bacteria biomass, separating the biomass from the culture medium and then freeze drying the separated biomass to obtain the dehydrated biomass.

3. A process according to claim 1 further comprising concentrating the separated biomass and then adding the cryoprotective agent to the concentrated biomass, and then adjusting the pH of the concentrated biomass and then freezing.

4. A process according to claim 2 further comprising concentrating the separated biomass and then freeze drying the concentrated biomass.

5. A process according to claim 1 or 2 wherein the culture medium further contains 0.05% to 0.5% by weight glucose and from about 1 mg/l $SO_2$ to 10 mg/l $SO_2$.

6. A process according to claim 1 or 2 wherein the culture medium has a pH of from about 3 to 4.5.

7. A process according to claim 1 or 2 further comprising fermenting a fermentable sugar with a yeast suitable for producing alcohol to prepare the culture medium.

8. A process according to claim 1 or 2 wherein the at least one malolactic bacterium strain is selected from the group consisting of *Leuconostoc oenos*, *Lactobacillus brevis* and *Lactobacillus plantarum*.

9. A process according to claim 1 or 2 wherein the at least one malolactic bacterium strain is *Leuconostoc oenos*.

10. A process according to claim 9 wherein the *Leuconostoc oenos* is selected from the group of strains consisting of CNCM I-1063, CNCM I-1064, CNCM I-1065 and CNCM I-1066.

11. A process according to claim 1 or 2 wherein the wine to which the biomass is added has been produced from a sugar-reduced must.

12. A process according to claim 1 or 2 wherein an alcohol content of the wine to which the biomass is added has been reduced prior to adding the biomass.

* * * * *

UNITED STATES PATENT AND TRADEMARK OFFICE
CERTIFICATE OF CORRECTION

PATENT NO. : 5,460,837
DATED : October 24, 1995
INVENTOR(S) : D'Amico et al.

It is certified that error appears in the above-indentified patent and that said Letters Patent is hereby corrected as shown below:

On the title page, item [75], Inventor's name "Thang H. Dac " should read
-- Thang Ho Dac --.

Signed and Sealed this

First Day of October, 1996

*Attest:*

BRUCE LEHMAN

*Attesting Officer*      *Commissioner of Patents and Trademarks*